US011610369B2

(12) United States Patent
Zagorchev et al.

(10) Patent No.: US 11,610,369 B2
(45) Date of Patent: Mar. 21, 2023

(54) AUTOMATIC EEG SENSOR REGISTRATION

(71) Applicant: KONINKLIJKE PHILIPS N.V., Eindhoven (NL)

(72) Inventors: Lyubomir Georgiev Zagorchev, Burlington, MA (US); Fabian Wenzel, Hamburg (DE); Nick Flaeschner, Hamburg (DE); Katerina Georgopoulou, Amsterdam (NL); Arne Ewald, Hamburg (DE); Shiv Sabesan, Pleasanton, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/283,853

(22) PCT Filed: Oct. 8, 2019

(86) PCT No.: PCT/EP2019/077167
§ 371 (c)(1),
(2) Date: Apr. 8, 2021

(87) PCT Pub. No.: WO2020/074480
PCT Pub. Date: Apr. 16, 2020

(65) Prior Publication Data
US 2021/0383603 A1 Dec. 9, 2021

Related U.S. Application Data

(60) Provisional application No. 62/743,364, filed on Oct. 9, 2018.

(51) Int. Cl.
*G06T 15/00* (2011.01)
*G06T 17/20* (2006.01)
(Continued)

(52) U.S. Cl.
CPC ............. *G06T 17/20* (2013.01); *G06T 7/344* (2017.01); *A61B 5/055* (2013.01); *A61B 5/291* (2021.01);
(Continued)

(58) Field of Classification Search
CPC ........... G06T 17/20; G06T 2207/10088; G06T 2210/41; G06T 2207/20081; G06T 7/344;
(Continued)

(56) References Cited

U.S. PATENT DOCUMENTS 5,568,816 A * 10/1996 Gevins ................. A61B 5/1077
600/544
5,817,029 A 10/1998 Gevins et al.
(Continued)

FOREIGN PATENT DOCUMENTS

CN 102708293 A 10/2012
WO 2016090239 A1 6/2016
(Continued)

OTHER PUBLICATIONS

Huang Y, Parra LC, Haufe S. The New York Head—A precise standardized vol. conductor model for EEG source localization and tES targeting. NeuroImage. Oct. 1, 20165; 140:150-62.*
(Continued)

*Primary Examiner* — Phu K Nguyen

(57) ABSTRACT

A method (10) that encodes electrode locations to a mean scalp mesh for adaptation to subsequent image scans.

17 Claims, 6 Drawing Sheets

(51) Int. Cl.
*G06T 7/33* (2017.01)
*A61B 5/291* (2021.01)
*A61B 5/055* (2006.01)

(52) U.S. Cl.
CPC ............... *G06T 2207/10088* (2013.01); *G06T 2207/20081* (2013.01); *G06T 2210/41* (2013.01)

(58) Field of Classification Search
CPC ......... A61B 5/055; A61B 5/369; A61B 5/291; A61B 5/4094; A61B 5/1077
USPC ....................................................... 345/418
See application file for complete search history.

(56) References Cited

U.S. PATENT DOCUMENTS

| | | | | |
|---|---|---|---|---|
| 6,052,619 | A * | 4/2000 | John | A61B 5/377 600/544 |
| 9,588,204 | B2 * | 3/2017 | Zagorchev | G01R 33/5608 |
| 9,761,005 | B2 * | 9/2017 | Tahmasebi Maraghoosh | G06T 7/344 |
| 10,438,345 | B2 * | 10/2019 | Wenzel | G06T 7/0012 |
| 2012/0245653 | A1 | 9/2012 | Bikson et al. | |
| 2014/0316230 | A1 * | 10/2014 | Denison | A61B 5/168 600/545 |
| 2016/0042524 | A1 | 2/2016 | Wenzel et al. | |
| 2016/0310070 | A1 * | 10/2016 | Sabesan | A61B 5/4094 |
| 2018/0184974 | A1 * | 7/2018 | Cimenser | A61B 5/38 |

FOREIGN PATENT DOCUMENTS

| | | |
|---|---|---|
| WO | 2017072706 A1 | 5/2017 |
| WO | 2018162307 A1 | 9/2018 |

OTHER PUBLICATIONS

Kabdebon C, Leroy F, Simmonet H, Perrot M, Dubois J, Dehaene-Lambertz G. Anatomical correlations of the international 10-20 sensor placement system in infants. Neuroimage. Oct. 1, 2014;99:342-56.*

Wachingerc, Golland P, Kremen W, Fischl B, Reuter M, Alzheimer's Disease Neuroimaging Initiative. BrainPrint: A discriminative characterization of brain morphology. NeuroImage. Apr. 1, 2015;109:232-48.*

Narizzano M, Arnulfo G, Ricci S, Toselli B, Tisdall M, Canessa A, Fato MM, Cardinale F. Seeg assistant: a 3DSlicer extension to support epilepsy surgery. BMC bioinformatics. Dec. 2017;18(1):1-3.*

Bikson M, Rahman A, Datta A, Fregni F, Merabet L. High-resolution modeling assisted design of customized and individualized transcranial direct current stimulation protocols. Neuromodulation. Jul. 2012;15(4):306-15.*

Cosandier-Rimélé, D., Merlet, I., Badier, J.M., Chauvel, p. and Wendling, F., 2008. The neuronal sources of EEG: modeling of simultaneous scalp and intracerebral recordings in epilepsy. NeuroImage, 42(1), pp. 135-146.*

Shahid S, Wen P, AhfockT. Assessment of electric field distribution in anisotropic cortical and subcortical regions under the influence of tDCS. Bioelectromagnetics. Jan. 2014;35(1):41-57.*

International Search Report and Written Opinion for International Application No. PCT/EP2019/077167, filed Oct. 3, 2019, 20 pages.

Sanchez-Todo, et al., "Personalization of hybrid brain models from neuroimaging and electrophysiology data", NeuroImage, Nov. 3, 2018, pp. 1-35.

Fleury, et al., "Automated Electrodes Detection during simultaneous EEG/fMRI", Mar. 2018, pp. 1-11 (Abstract).

Tian, et al., "A study on the neural mechanism of inhibition of return by the even-related potential in the Go/Nogo task", Biological Psychology, vol. 79, No. 2 Oct. 1, 2008, pp. 171-178. (Abstract).

Noblet, et al., "Symmetric Nonrigid Image Registration: Application to Average Brain Templates Construction", Medical Image Computing and Computer-Assisted Intervention, Proceedings 11th International Conference, MICCAI 2008, Sep. 6, 2008, pp. 897-904.

Vainshenker, et al., "EEG Reflection of Clinical Effects Dynamics during Botulinum Toxin Therapy of Movement Disorders under Long-Term Consciousness Disorders", Human Physiology, vol. 44, No. 2, May 4, 2018, p. 218. (Abstract).

Yin Tian, et al., "Differential consequences of orienting attention in parallel and serial search: An ERP study", Brain Research, Elsevier, Amsterdam, NL, vol. 1391, Mar. 24, 2011, pp. 87-88.

Richards, et al., "Evaluating Methods for Construction Average High-Density Electrode Positions", Brain Topography, Human Sciences Press, New York, NY, vol. 28, No. 1, Sep. 19, 2014, pp. 70-86.

Wenzel, et al., "Rapid fully automatic segmentation of subcortical brain structures by shape-constrained surface adaptation", Medical Image Analysis, Feb. 23, 2018, 52 pages.

* cited by examiner

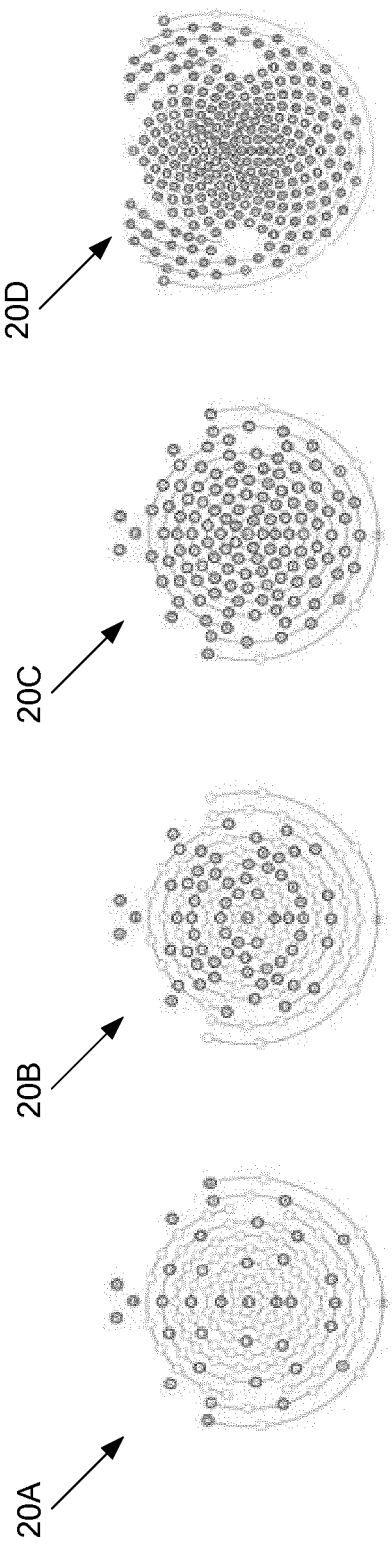
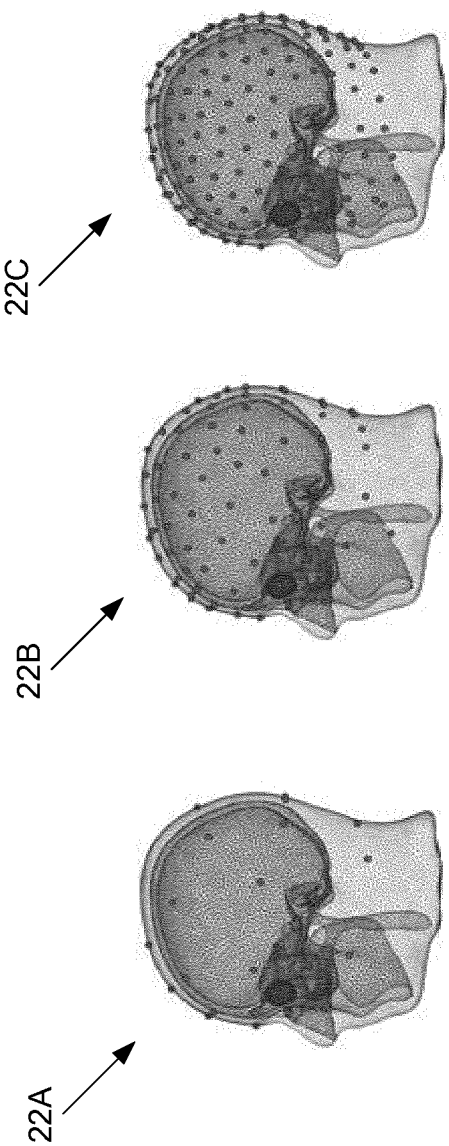

AUTOMATIC EEG SENSOR REGISTRATION

RELATED APPLICATIONS

This application is the U.S. National Phase application under 35 U.S.C. § 371 of International Application No. PCT/EP2019/077167, filed on Oct. 8, 2019, which claims priority to and the benefit of Provisional Application No. 62/743,364, filed Oct. 9, 2018, which is incorporated by reference in its entirety.

FIELD OF THE INVENTION

The present invention is generally related to quick and accurate placement of electroencephalogram (EEG) electrodes on a subject's skull.

BACKGROUND OF THE INVENTION

The complex pathophysiology of epilepsy has emphasized the need for structural and functional analysis of brain regions and their dynamic interactions. Electrical source imaging (ESI) is a technique that estimates the location of sources responsible for scalp potentials as measured by electroencephalogram (EEG) electrodes positioned on the scalp. ESI is obtained by formulating a forward model that describes how electrical potential generated by the source propagates to the scalp, and solving an inverse problem that provides mapping of measured scalp potentials to estimated sources. Precise brain tissue segmentation and electrical conductivity values are necessary for accurate forward solution. As a result, ESI is moving from generic and conformal atlases to patient-specific head models derived from individual MRIs. Currently, the registration of EEG electrodes to a magnetic resonance imaging (MRI) scan is a tedious and semi-automatic process that involves a number of manual steps.

Some progress has been made to alleviate the manual burden. For instance, in "Automated Electrodes Detection during Simultaneous EEG/fMRI" by Fleury et al., first posted online on Aug. 20, 2018 and reprinted by bioRxiv, the authors describe a fully automated method for the detection and labeling of an MR compatible EEG cap into the MR space. The retrieval of electrodes includes providing a mask that includes a volume where the electrodes reside and then performing electrode detection inside this volume (volume of interest or VOI). To extract the VOI, an outskin mask is performed from a T1 image, a dilation and removal of the mask is performed to obtain the layer where the electrodes are located, and then a masking operation between an ultra-short echo time (UTE) image and the VOI results in the VOI. A 3D Hough transform is used to segment the electrodes inside the VOI, providing a list of potential electrodes. The electrodes are filtered using iterative closest point (ICP), leading to the position of the electrodes on a subject.

SUMMARY OF THE INVENTION

One object of the present invention is to reduce the manual or semi-automatic burdens involved with registering electrodes to image scans. To better address such concerns, in a first aspect of the invention, an apparatus that encodes electrode locations to a mean scalp mesh for adaptation to subsequent image scans. This apparatus provides a fully automated process to identify electrodes on an image scan in a matter of seconds, which enables clinically acceptable volumetric electrical source imaging (ESI).

In one embodiment, the apparatus is configured to receive an average electrode file corresponding to averages of plural electrode locations; register the average electrode locations to plural vertices of a mean scalp mesh; enforce symmetry; and provide the mean scalp mesh encoded with the electrode locations based on the registration and enforcement. Through these functions, a model is generated that facilitates an automated process of electrode identification for individualized imaging scans.

In one embodiment, the apparatus is configured to enforce symmetry either for a subset of the registered electrode locations that are not symmetrical, by making the average electrode positions symmetric, or by making the plural vertices of the mean scalp mesh symmetric. Thus, through enforcement of symmetry, there is confidence that electrodes are located on the mean scalp mesh and the model is thus adaptable to an individual MRI scan for extraction of electrode locations.

In one embodiment, the apparatus is configured to receive, register, enforce, and provide once during a training phase, and wherein at least the registering and enforcing are performed automatically. By automating all or a portion of the apparatus functions, a reduction in the typically labor-intensive electrode registration process is realized.

In one embodiment, the apparatus is configured to receive a deformable head model comprising a mean scalp mesh encoded with electrode locations; adapt the deformable head model to an imaging scan; and extract locations of the electrodes based on the adaptation. The application of the deformable head model established through the training stage results in a process that identifies electrodes for individualized MRI scans quickly and with reduced burden on technicians or medical professionals.

In one embodiment, the apparatus is configured to adapt the deformable head model by deforming a mean mesh of the deformable head model to match information pertaining to the imaging scan, wherein the adapting and extracting is achieved automatically. Again, the automation of this electrode identification process alleviates the burden on technicians and professionals alike.

In one embodiment, the apparatus is configured to provide an output of the electrode locations, wherein the output comprises one or any combination of electrode coordinates, a visualization of the electrode coordinates, a visualization of subject's head corresponding to the imaging scan and the electrodes projected onto the head. The visualization facilitates adjustment and/or correction of the electrode net.

In one embodiment, the apparatus is configured to adapt the deformable head model based on aligning vertices of the mean scalp mesh with landmarks corresponding to anatomical structures. The use of landmarks enables a reduction or avoidance of errors in electrode placement.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

FIGS. 2A-2D are schematic diagrams of average electrode locations from an average electrode file for various types of electrode configurations, in accordance with an embodiment of the invention.

FIGS. 3A-3C are schematic diagrams of encoded electrode locations on a head model for various electrode configurations based on registering a mean scalp mesh to the average electrode locations along with symmetry enforcement, in accordance with an embodiment of the invention.

DETAILED DESCRIPTION OF EMBODIMENTS

Figure 1:
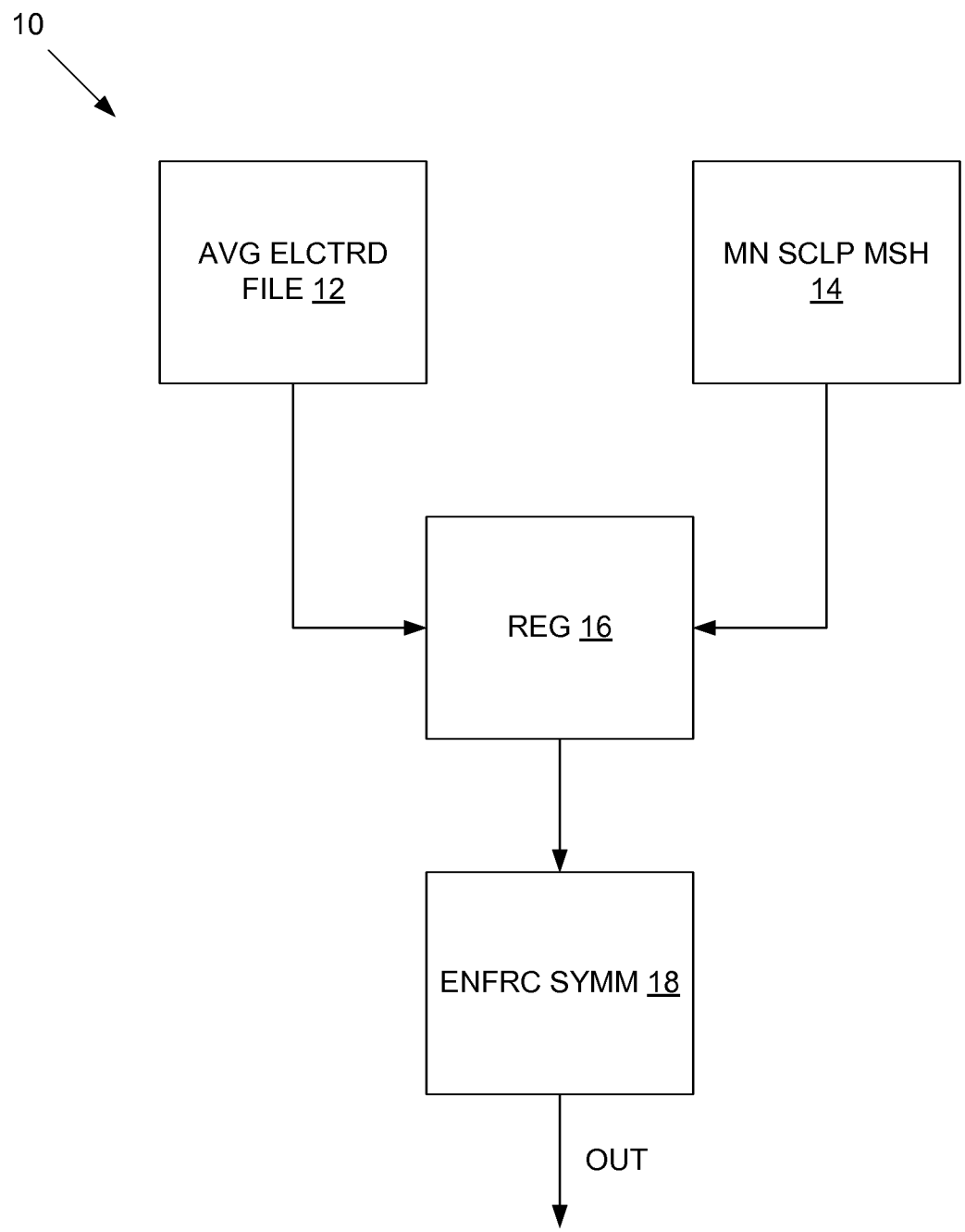
FIG. 1 is a flow diagram that illustrates an example method for registering electrodes to a mean scalp mesh during a training stage, in accordance with an embodiment of the invention.

Disclosed herein are certain embodiments of an electrode encoding apparatus and methods that encode a mean scalp mesh with electrode locations and then adapt a head model comprising the mean scalp mesh to subject-specific imaging scans. In one embodiment, an electrode encoding method implements a training stage for implementing registration of the mean scalp mesh to an average electrode file and enforces symmetry to derive the mean scalp mesh with the encoded electrode locations. In some embodiments, an electrode encoding method is implemented in an application stage where the method adapts the mean scalp mesh to an individual's imaging scan and extracts the (estimated) electrode locations based on the adaptation.

Digressing briefly, epileptic seizures are caused by uncontrolled electrical discharges originating from specific regions in the human brain. While structural Magnetic Resonance Imaging (MRI) is a routine modality of choice in standard clinical assessment, it is often non-revealing in epileptic subjects. The electrical activity of seizures can be monitored effectively using electroencephalography (EEG), but EEG lacks spatial resolution and needs to be aligned with structural MRI for volumetric electrical source imaging (ESI). This alignment or registration is an arduous process. Some techniques have been developed to streamline certain processes, such as discussed in the background. In certain embodiments disclosed herein, electrode encoding methods are described that can simplify and streamline user workflow and enable clinically acceptable ESI.

Having summarized certain features of electrode encoding methods of the present disclosure, reference will now be made in detail to the description of electrode encoding methods as illustrated in the drawings. While electrode encoding methods will be described in connection with these drawings, there is no intent to limit it to the embodiment or embodiments disclosed herein. For instance, examples are provided that use a single apparatus for one method deriving a mean scalp mesh with encoded electrode locations in a training stage and then, in an application stage, another method for adapting a deformable head model comprising the mean scalp mesh with encoded electrode locations to an imaging scan of a given subject and extracting the electrode locations. However, in some embodiments, the independent training and application stages may be carried out in separate devices, or implemented among a plurality of devices (e.g., distributed processing system) in some embodiments. Further, although the description identifies or describes specifics of one or more embodiments, such specifics are not necessarily part of every embodiment, nor are all of any various stated advantages necessarily associated with a single embodiment. On the contrary, the intent is to cover all alternatives, modifications and equivalents included within the principles and scope of the disclosure as defined by the appended claims. For instance, two or more embodiments may be interchanged or combined in any combination. Further, it should be appreciated in the context of the present disclosure that the claims are not necessarily limited to the particular embodiments set out in the description.

FIG. 1 is a flow diagram that illustrates an embodiment of an example method for registering electrodes to a mean scalp mesh during a training stage. It should be appreciated that the method depicted in FIG. 1 is one illustrative example, and that in some embodiments, a different number of steps or functions may be implemented. The method, denoted as method 10, comprises receiving an average electrode file corresponding to (respective) averages of plural electrode locations (AVG ELCTRD FILE) 12, receiving a mean scalp mesh (MN SCLP MSH) 14, registering the average electrode locations to plural vertices of the mean scalp mesh (REG) 16, enforcing symmetry for a subset of the registered locations that are not symmetrical (ENFRC SYMM) 18, and providing an output (OUT). For instance, the output may comprise a deformable head model that includes the mean scalp mesh with the marked or encoded electrode locations (e.g., at plural vertices). The output may be stored as a file in local or remote memory for adaptation during an application stage as explained in association with FIG. 4.

Referring further to the method 10 of FIG. 1, the average electrode file 12 is generated based on comprehensive head-imaging of plural (e.g., a large population) subjects wearing various arrangements/configurations of electrodes. In one embodiment, the imaging may be accomplished through the use of a multi-stereo camera system, such as a large geodesic dome of cameras (e.g., Philips' GPS system) that takes eleven photos simultaneously to record the position of up to 256 electrodes on a subject's head. In some embodiments, other imaging mechanisms may be used. FIGS. 2A-2D provide an illustration of different arrangements of electrodes 20 (e.g., 20A-20D) from the average electrode file, including electrode coordinates 20A for 32 (FIG. 2A), 20B for 64 (FIG. 2B), 20C for 128 (FIG. 2C), and 20D for 256 (FIG. 2D) electroencephalogram (EEG) electrode configurations. The GPS software uses a semi-automated algorithm to create a 3D point cloud of electrode or sensor locations (herein, electrode and sensor are terms that are used interchangeably).

The mean scalp mesh 14 is based on imaging scans (e.g., magnetic resonance imaging (MRI) scans) of the plural subjects. That is, each scalp mesh is derived from a shape-constrained deformable brain model that is segmented into a set of cortical and sub-cortical brain regions. Stated otherwise, the brain model consists of a set of triangular meshes that provide point-based correspondence from one subject to another. Examples of suitable brain models are described in L. Zagorchev, A. Goshtasby, K. Paulsen, T. McAllister, S. Young, and J. Weese, Manual annotation, 3-D shape reconstruction, and traumatic brain injury analysis, Int'l Workshop Multimodal Brain Image Analysis (MBIA), Toronto, Calif., September 2011, and L. Zagorchev, C. Meyer, T. Stehle, R. Kneser, S. Young, and J. Weese, Evaluation of Traumatic Brain Injury patients using a shape-constrained deformable model, Int'l Workshop Multimodal Brain Image Analysis (MBIA), Toronto, Calif., September 2011. Other models are also contemplated herein. The mean scalp mesh 14 comprises a 3D point cloud that will be registered with the 3D point cloud of the average electrode locations.

The registration 16 of average EEG electrode locations to the mean scalp mesh may be viewed as an alignment of the two aforementioned point clouds. The average electrode coordinates 20 for 32, 64, 128, and 256 EEG sensor configurations of FIGS. 2A-2D may be aligned to the mean scalp mesh with a point based rigid registration (e.g., a manually initialized, iterative closest point registration). That is, after the EEG electrode locations are aligned with the mean scalp mesh, vertices from the mean scalp mesh closest to the EEG electrodes may be selected and saved as point landmarks (i.e., the electrodes become landmarks after being marked or encoded on the mesh). These electrode locations comprise an estimation of the most probable location. In one embodiment, during this training stage, the registration is performed just once to encode the electrodes as point landmarks on the mean scalp mesh. In effect, the mean (scalp) mesh is used to generate a model of mean electrode positions on an average head. Note that the terms scalp mesh and skin mesh are used interchangeably herein. This mean (scalp) mesh is adapted to an individual's head based on an MRI scan, the resultant mesh comprising an individualized mesh.

Note that in some embodiments, during the process of registration 16 and/or during adaptation to an individual head, there may be (automatic) enforcement of certain electrodes to anatomical landmarks. For instance, dedicated vertices of the mean scalp mesh may be specifically aligned with anatomical landmarks, including the nasion, inion, and common landmarks near the left and right ears. The registration 16 comprises a fully-automatic alignment of specific vertices of the mean scalp mesh with landmarks in the MRI scan. Known detectors for anatomical landmarks in medical images exist and may be implemented by artificial intelligence (AI), including via a localization network or by other means. In one embodiment, through this refined registration embodiment, the mean scalp mesh is adapted to the MRI scans such that the specific subset of vertices match their intended anatomic position. In some embodiments (e.g., after registration), the mesh is similarly adapted to an individual's MRI scan so the specific subset of vertices match their intended anatomic position. A focus here is on landmarks that may be detected anatomically, since many electrode positions cannot be identified as anatomical landmarks since there are no specific features at those individual positions.

As to the enforcement of symmetry 18, in one embodiment, the symmetry of electrode locations with respect to the mid-sagittal plane may be enforced by comparing electrode locations on the right hemisphere with their corresponding electrode locations on the left hemisphere. The difference between a pair of electrodes in all three directions may be split in half to obtain the new symmetric sensor locations on the mean scalp mesh. In other words, the coordinates (e.g., X, Y, Z) of the electrodes should be symmetric with respect to the mid-sagittal plane, since the brain is likewise symmetric with respect to the mid-sagittal plane. This process merely enforces symmetry (e.g., where symmetry is absent) by adjusting the coordinates of each pair of electrodes. FIGS. 3A-3C illustrate symmetric electrode maps 22 (e.g., 22A-22C) for different electrode configurations. For instance, FIGS. 3A-3C show symmetric electrode locations encoded as point landmarks on the mean scalp mesh of the head model, including map 22A for 32, map 22B for 128, and map 22D for 256 EEG sensor net configurations, respectively. These maps 22 of symmetric electrodes encoded as point landmarks on the mean scalp mesh of the head model are output to another component or device, including memory, another module, etc.

Note that variations to the method 10 depicted in FIG. 1 are contemplated to be within the scope of the disclosure. For instance, in some embodiments, the enforcement of symmetry may be out of the order depicted in FIG. 1, and may involve other techniques. For instance, in the average electrode positions may be made symmetric first (e.g., without an average skin mesh) by mirroring coordinates along the left-right (L-R) axis. As another example, the vertices of the average skin mesh may be made symmetric (without average electrode positions) by mirroring coordinates along the L-R axis in some embodiments. Accordingly, symmetry enforcement according to these other mechanisms results in symmetric locations on the mean mesh as well.

Figure 4:
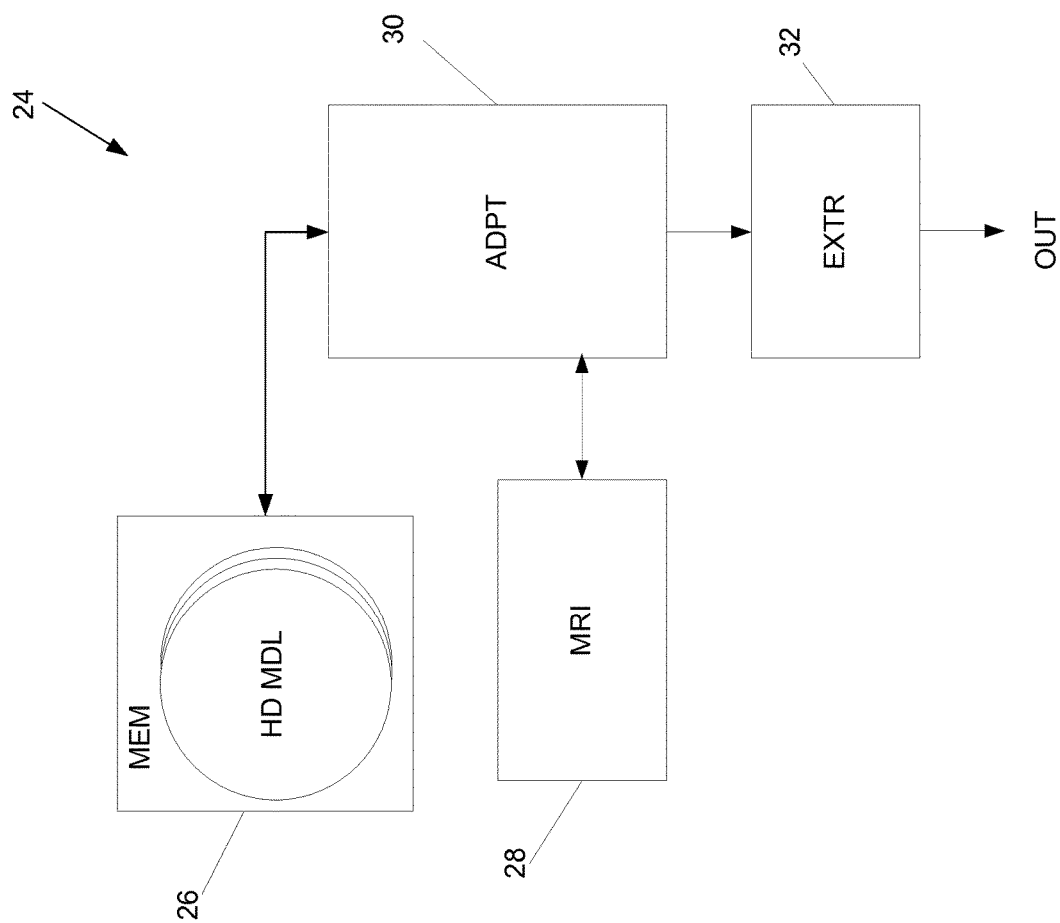
FIG. 4 is a flow diagram that uses encoded electrode locations, derived from a training stage, in an application stage to locate or extract the electrodes on an image scan of a subject, in accordance with an embodiment of the invention.

Having described an example training stage for an embodiment of an electrode encoding method 10, attention is now directed to FIG. 4, which is a flow diagram that illustrates an embodiment of an example method 24 that adapts the deformable head model, having the mean scalp mesh encoded with electrode locations and derived from the training stage, to subject-specific imaging scans to extract electrode locations during an application stage. The method 24 comprises receiving a deformable head model having a mean scalp mesh with encoded electrode locations (HD MDL) 26, receiving an imaging scan (MRI) 28 for a subject, adapting the deformable head model to the imaging scan (ADPT) 30, extracting locations of the electrodes based on the adaptation (EXTR) 32, and providing an output (OUT).

Figure 5:
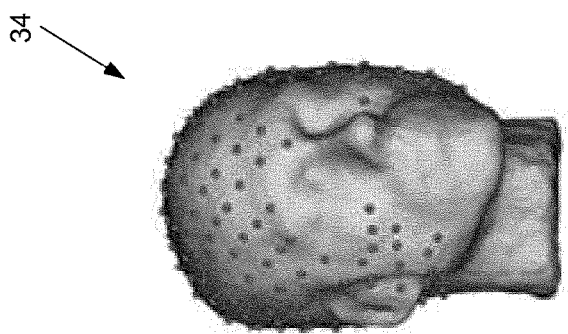
FIG. 5 is a schematic diagram that shows electrode locations for a subject-specific image scan, in accordance with an embodiment of the invention.

In one embodiment, the deformable head model comprises the output of the method 10 (FIG. 1). The MRI scan 28 is specific to a particular subject. The adaptation of the head model to a new scan 30 automatically deforms the mean scalp mesh to match the patient's data/shape and defines patient specific electrode locations. The point landmarks can be extracted 32 after model adaptation to provide EEG electrode locations aligned with the MRI scan, as shown in example output 34 of FIG. 5. Though the output is depicted as an image overlaid with the electrodes, in some embodiments, the output may merely be the electrode locations (e.g., X, Y, Z coordinates), or a combination of both. In some embodiments, the output may include a visualization that includes the estimated electrode positions on top of the segmented skin using known 3D visualization techniques. In some embodiments, visualization may include immersive-type techniques, including augmented reality, to superimpose the estimated electrode locations on the skin of a subject (e.g., as viewed via a smartphone camera, head-mounted display, etc.).

Note that, as mentioned above, the adaptation (or in some embodiments, a post-processing step) may involve the alignment of dedicated vertices of the skin mesh with anatomical landmarks including the nasion, inion, and common landmarks near the left and right ears. In other words, landmark identification may be performed in the training stage, omitted in the training stage, or used in both training and application stages. This adaptation may include local, surface-specific constraint terms that minimize spatial variability of corresponding skin vertices. After alignment, individual vertices of a mesh representing the skin surface may be identified to represent electrodes, after modeling their spatial variability with respect to the segmented skin using hand-held optical measurements or photogrammetry (e.g., Philips GPS system), among other techniques.

Figure 6:
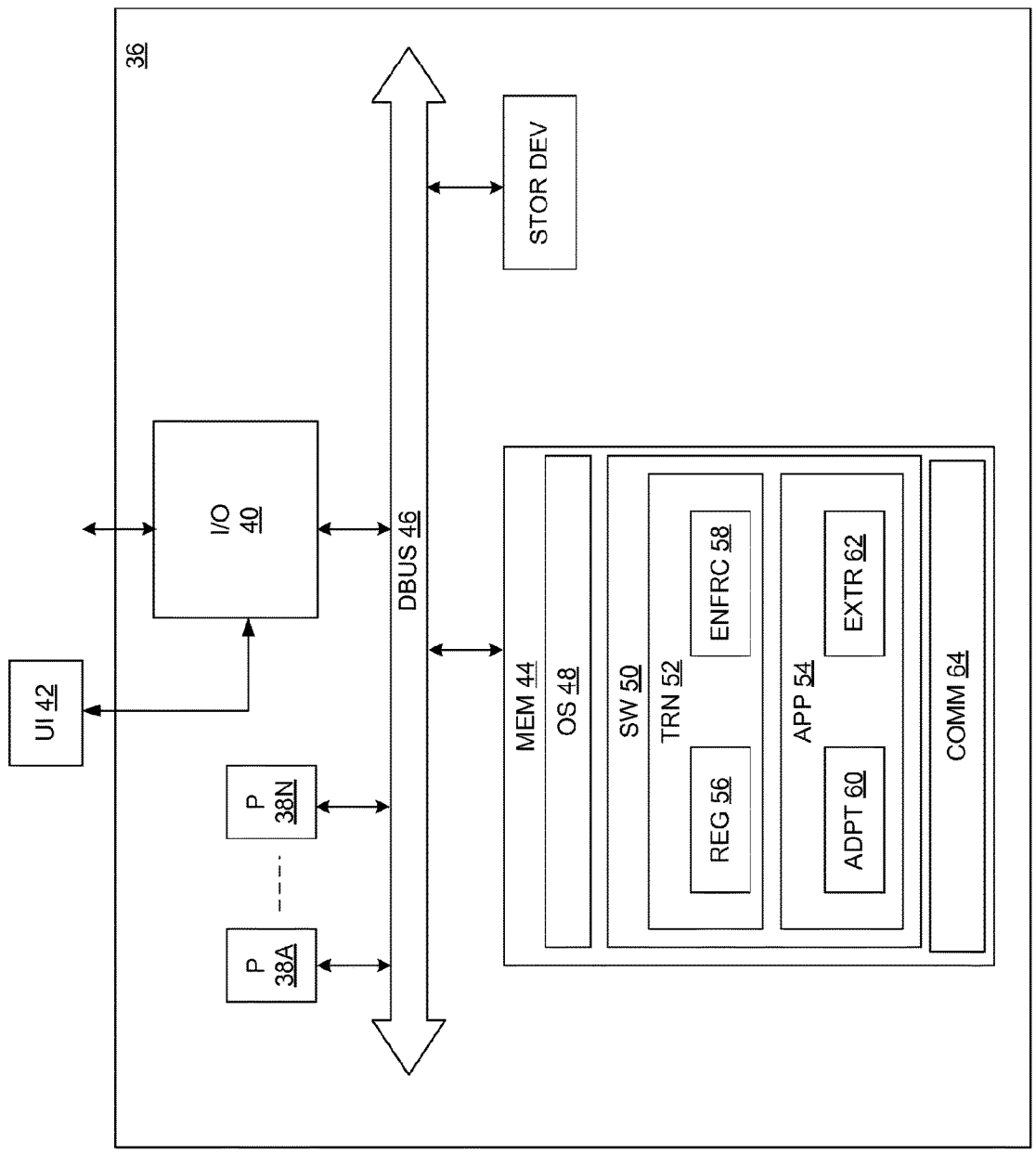
FIG. 6 is a block diagram that illustrates an example apparatus that encodes electrodes during a training stage and adapts the encoded electrodes for a patient-specific image scan in an application stage, in accordance with an embodiment of the invention.

Having described certain embodiments of electrode encoding methods, attention is directed to FIG. 6, which illustrates an embodiment of an example apparatus 36 for performing the electrode encoding methods 10 and/or 24. In the depicted embodiment, functionality of the electrode encoding methods is implemented as an apparatus comprising co-located software and hardware components collectively embodied as a computing device (which may include a medical device). It should be appreciated that, in some embodiments, the functionality of the electrode encoding methods may be performed in one or more devices that reside local to an imaging machine or system or that reside remote from the imaging machine/system (e.g., in a cloud-based platform, server farm, web servers, application server, etc.). In some embodiments, plural devices remote from each other (e.g., client-server relationship) may collectively perform the functionality of the electrode encoding method in distributed processing fashion. One having ordinary skill in the art should appreciate in the context of the present disclosure that the example apparatus, herein referred to as computing device 36, is merely illustrative of one embodiment, and that some embodiments of computing devices may comprise fewer or additional components, and/or some of the functionality associated with the various components depicted in FIG. 6 may be combined, or further distributed among additional modules or computing devices, in some embodiments. It should be appreciated that certain well-known components of computer systems are omitted here to avoid obfuscating relevant features of the computing device 36.

In one embodiment, the computing device 36 comprises one or more processors (P) 38 (e.g., 38A . . . 38N), input/output (I/O) interface(s) 40 (I/O), one or more user interfaces (UI) 42, which may include one or more of a keyboard, mouse, microphone, speaker, display, etc.), and memory 44 (MEM), all coupled to one or more data busses, such as data bus 46 (DBUS). In some embodiments, the user interfaces may be coupled directly to the data bus 46. The memory 44 may include any one or a combination of volatile memory elements (e.g., random-access memory RAM, such as DRAM, and SRAM, etc.) and nonvolatile memory elements (e.g., ROM, Flash, solid state, EPROM, EEPROM, hard drive, tape, CDROM, etc.). The memory 44 may store a native operating system, one or more native applications, emulation systems, or emulated applications for any of a variety of operating systems and/or emulated hardware platforms, emulated operating systems, etc. In some embodiments, a separate storage device (STOR DEV) may be coupled to the data bus 46 or as a network-connected device (or devices) via the I/O interfaces 40 and one or more networks. In the depicted embodiment, the computing device 36 may be coupled to an imaging system via the I/O interfaces, though it should be appreciated that the connection may be achieved via one or more networks in some embodiments or according to other known connections or interconnections. The storage device may be embodied as persistent memory (e.g., optical, magnetic, and/or semiconductor memory and associated drives). In some embodiments, the storage device or memory 44 may store a model bank, scans, among other subject information.

In the embodiment depicted in FIG. 6, the memory 44 comprises an operating system 48 (OS) (e.g., LINUX, macOS, Windows, etc.), and electrode encoding software (SW) 50, which includes a training module (TRN) 52 and an application module (APP) 54. The training module 52 comprises a registration module (REG) 56 and a symmetry enforcement module (ENFRC) 58. The application module 54 comprises an adaptation module (ADPT) 60 and an extraction module (EXTR) 62. In some embodiments, there may be fewer or additional modules. The modules are depicted in this example as blocks of instructions (e.g., executable code) in the form of software/firmware (including middleware or microcode), though in some embodiments, functionality of the same may be implemented via hardware (e.g., circuitry, including application-specific integrated circuits (ASICs), field programmable gate arrays (FPGAs), vector processors, tensor processing units, etc.). Functionality of the electrode encoding software 50, including the training module 52 (further including the registration module 56 and the symmetry enforcement module 58) and the application module 54 (further including the adaptation module 60 and the extraction module 62) collectively perform the respective functionality described in and in association with method 10 (FIG. 1) and method 24 (FIG. 4). For instance, the training module 52 may perform the functionality associated with method 10, with functionality of the registration module 56 and the symmetry enforcement module 58 performing the functionality of the registration 16 and enforce symmetry 18 functions or steps. Similarly, the application module 54 may perform the functionality associated with method 24, with the adaptation module 60 and extraction module 62 performing the functionality associated with adaptation 30 and extraction 32. In some embodiments, there may be fewer or additional modules. The memory 44 further comprises a communications module (COMM) 64. The communications module 64 comprises software/firmware that is configured to enable the communication of information (via the I/O interfaces 40) among other systems and/or devices.

Note that the memory 44 and storage device may each be referred to herein as a non-transitory, computer readable storage medium or the like.

Execution of the processing software 50, including the training module 52 (further including the registration module 56 and the symmetry enforcement module 58) and the application module 54 (further including the adaptation module 60 and the extraction module 62), may be implemented by the one or more processors 38 under the management and/or control of the operating system 48. The processor(s) 38 may be embodied as a custom-made or commercially available processor, including a single or multi-core central processing unit (CPU), tensor processing unit (TPU), graphics processing unit (GPU), vector processing unit (VPU), or an auxiliary processor among several processors, a semiconductor based microprocessor (in the form of a microchip), a macroprocessor, one or more application specific integrated circuits (ASICs), field programmable gate arrays (FPGUs), a plurality of suitably configured digital logic gates, and/or other known electrical configurations comprising discrete elements both individually and in various combinations to coordinate the overall operation of the computing device 36.

The I/O interfaces 40 comprise hardware and/or software to provide one or more interfaces to other systems or devices. The I/O interfaces 40 may include a cable and/or cellular modem, and/or establish communications with other devices or systems via an Ethernet connection, hybrid/fiber coaxial (HFC), copper cabling (e.g., digital subscriber line (DSL), asymmetric DSL, etc.), using one or more of various communication protocols (e.g., TCP/IP, UDP, etc.). In general, the I/O interfaces 40, in cooperation with the communications module 64 comprises suitable hardware to enable communication of information via PSTN (Public Switched Telephone Networks), POTS, Integrated Services Digital Network (ISDN), Ethernet, Fiber, DSL/ADSL, Wi-Fi, cellular (e.g., 3G, 4G, 5G, Global System for Mobile Communications (GSM), General Packet Radio Service (GPRS), etc.), Bluetooth, near field communications (NFC), Zigbee, among others, using TCP/IP, UDP, HTTP, DSL. The user interfaces 42 may include a keyboard, mouse, microphone, display, immersive head set, etc., which enable input and/or output by an administrator or other user. In some embodiments, the user interfaces 42 may cooperate with associated software to enable augmented reality or virtual reality, or visualization may be achieved in connection with other devices via the I/O interfaces 40.

When certain embodiments of the computing device 36 are implemented at least in part with software (including firmware, middleware, microcode, etc.), it should be noted that the software (e.g., the training module 52 (further including the registration module 56 and the symmetry enforcement module 58) and the application module 54 (further including the adaptation module 60 and the extraction module 62) can be stored on a variety of non-transitory computer-readable (storage) medium for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the computing device 36 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), TPUs, GPUs, and/or other accelerators/co-processors, etc.

Figure 7:
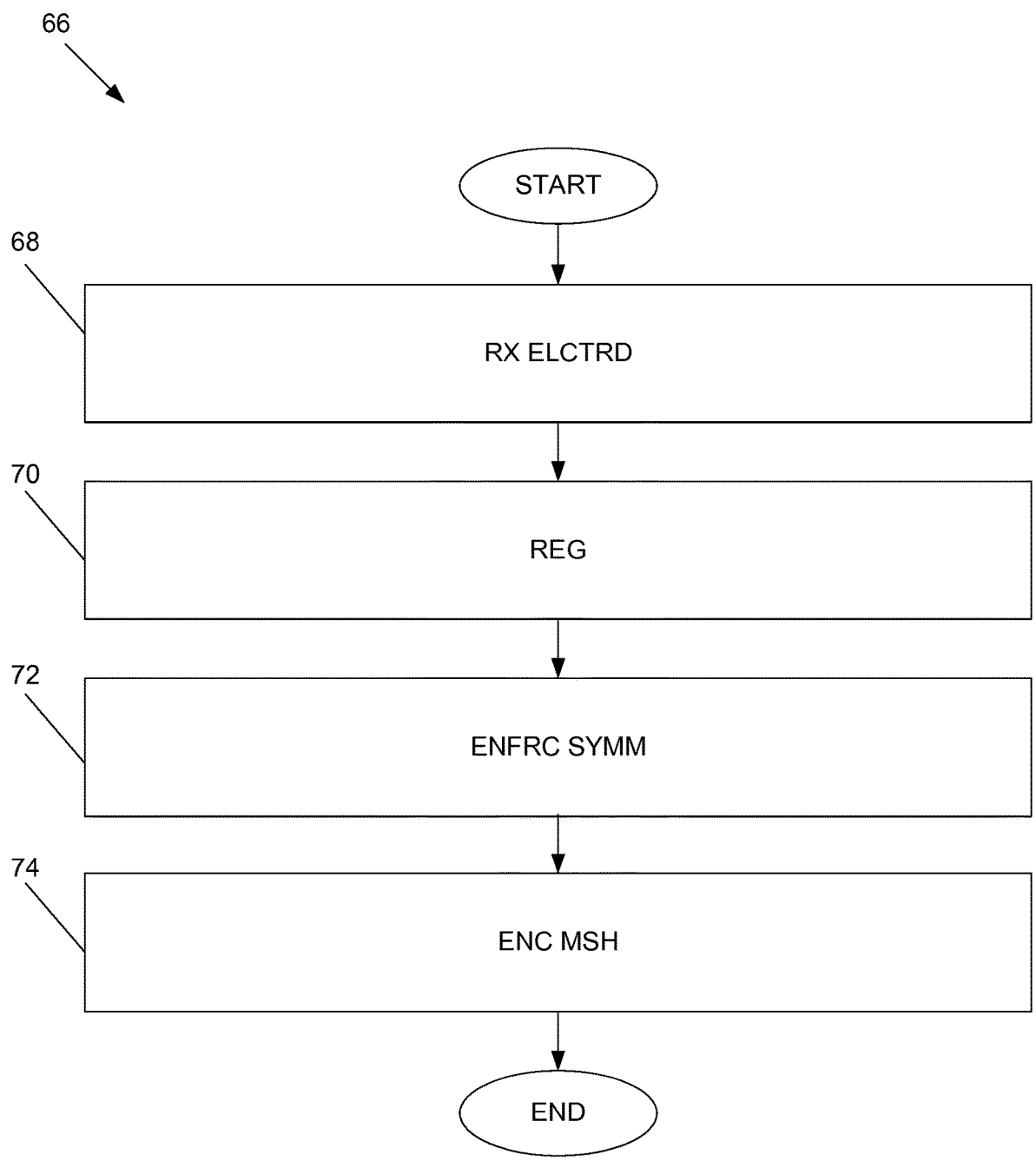
FIG. 7 is a flow diagram that illustrates an example electrode encoding method, in accordance with an embodiment of the invention.

Having described certain embodiments of an electrode encoding apparatus and methods, it should be appreciated that an example electrode encoding method pertaining to a training stage, depicted in FIG. 7 and denoted as method 66, which is shown bounded by a start and end, comprises receiving an average electrode file corresponding to averages of plural electrode locations (RX ELCTRD) (68); registering the average electrode locations to plural vertices of a mean scalp mesh (REG) (70); enforcing symmetry for a subset of the registered electrode locations that are not symmetrical (ENFRC SYMM) (72); and providing the mean scalp mesh encoded with the electrode locations based on the registration and enforcement (ENC MSH) (74). As explained above, variations to the method 66 may be implemented in some embodiments, including establishing symmetric average electrode positions, symmetric vertices of the average skin mesh, registering with or without the use of landmarks, etc.

Figure 8:
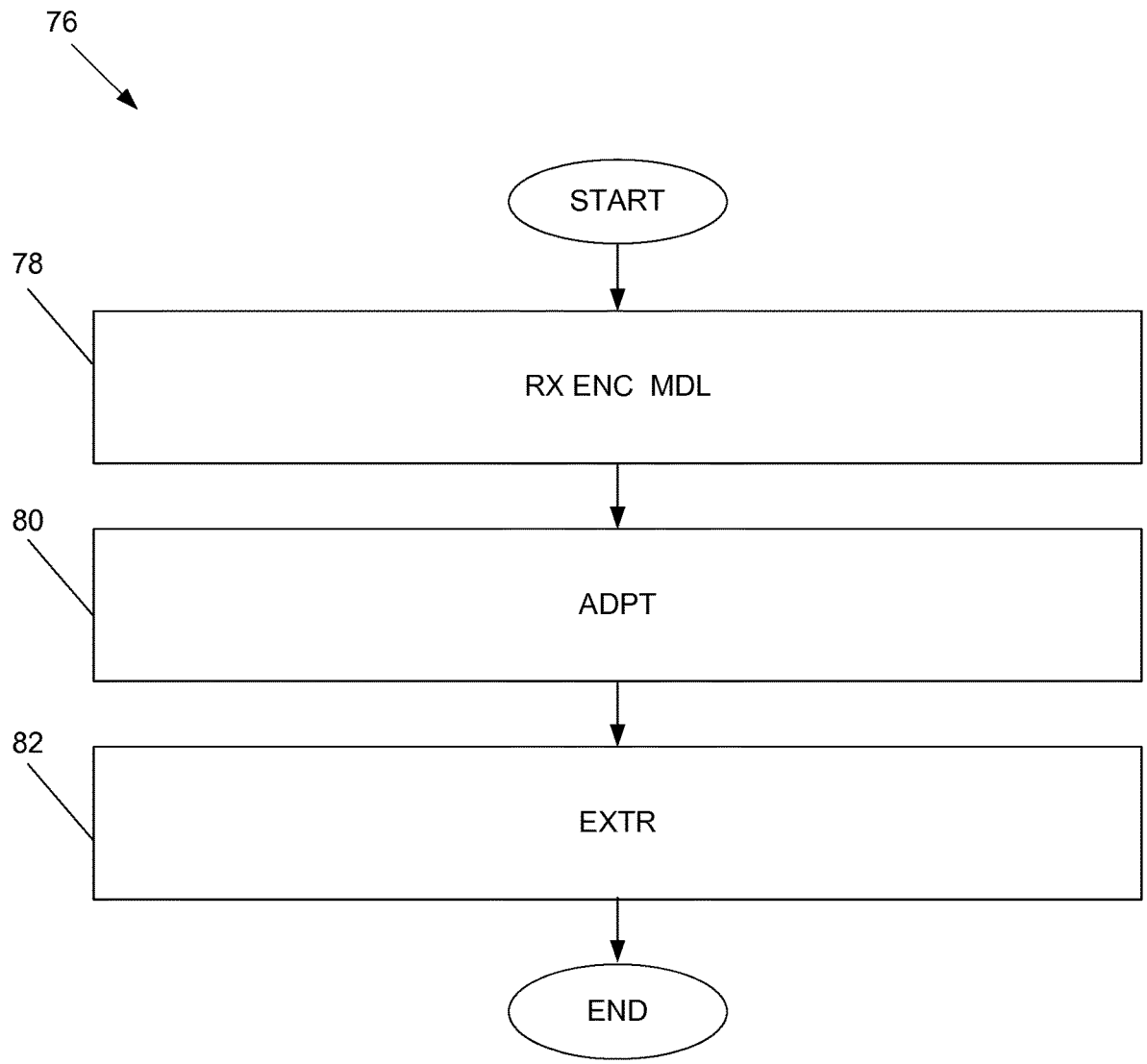
FIG. 8 is a flow diagram that illustrates an example method for electrode placement based on encoded electrodes, in accordance with an embodiment of the invention.

In another embodiment pertaining to an application stage, a method 76, depicted in FIG. 8 and bounded by a start and end, comprises receiving a deformable head model comprising a mean scalp mesh encoded with electrode locations (RX ENC MDL) (78); adapting the deformable head model to an imaging scan (ADPT) (80); and extracting locations of the electrodes based on the adaptation (EXTR) (82). As explained above, adaptation may include alignment of vertices with anatomical landmarks.

Note that the methods 66 and 76 may be implemented by the apparatus 36, or by plural devices in some embodiments.

Any process descriptions or blocks in flow diagrams should be understood as representing modules, segments, or portions of code which include one or more executable instructions for implementing specific logical functions or steps in the process, and alternate implementations are included within the scope of the embodiments in which functions may be executed out of order from that shown or discussed, including substantially concurrently or in reverse order, depending on the functionality involved, as would be understood by those reasonably skilled in the art of the present disclosure. In some embodiments, one or more steps may be omitted, or further steps may be added.

In one embodiment, an apparatus is disclosed, comprising: a memory comprising instructions; and one or more processors configured by the instructions to: receive an average electrode file corresponding to averages of plural electrode locations; register the average electrode locations to plural vertices of a mean scalp mesh; enforce symmetry; and provide the mean scalp mesh encoded with the electrode locations based on the registration and enforcement.

The preceding apparatus, wherein the one or more processors are further configured by the instructions to register at least a portion of the average electrode locations based on landmarks corresponding to anatomical structures.

Any one of the preceding apparatuses, wherein the one or more processors are further configured by the instructions to enforce symmetry either for a subset of the registered electrode locations that are not symmetrical, by making the average electrode positions symmetric, or by making the plural vertices of the mean scalp mesh symmetric.

Any one of the preceding apparatuses, wherein the one or more processors are further configured by the instructions to register the average electrode locations based on a point based rigid registration.

Any one of the preceding apparatuses, wherein the one or more processors are further configured by the instructions to enforce symmetry with respect to a mid-sagittal plane of the mean scalp mesh by: comparing corresponding electrode locations across the mid-sagittal plane; and generating new electrode locations on the mean scalp mesh based on a half of a difference between a pair of electrode location in three dimensions.

Any one of the preceding apparatuses, wherein the receiving, registering, enforcing, and providing are performed once during a training phase, and wherein at least the registering and enforcing are performed automatically.

In one embodiment, a method is disclosed for performing the receiving, registering, enforcing, and providing of any one of the preceding apparatuses.

In one embodiment, a non-transitory, computer readable storage medium is disclosed comprising instructions that when executed by one or more processors, causes the one or more processors to perform the receiving, registering, enforcing, and providing of any one of the preceding claims.

In one embodiment, an apparatus is disclosed, comprising: a memory comprising instructions; and one or more processors configured by the instructions to: receive a deformable head model comprising a mean scalp mesh encoded with electrode locations; adapt the deformable head model to an imaging scan; and extract locations of the electrodes based on the adaptation.

In one embodiment, the receding apparatus, wherein the imaging scan comprises a magnetic resonance imaging scan of a subject, and wherein the deformable head model with encoded electrodes is based on an a priori training stage.

In one embodiment, any one of the preceding apparatuses, wherein the one or more processors are configured by the instructions to adapt the deformable head model by deforming a mean mesh of the deformable head model to match information pertaining to the imaging scan, wherein the adapting and extracting is achieved automatically.

In one embodiment, any one of the preceding apparatuses, wherein the one or more processors are configured by the instructions to provide an output of the electrode locations, wherein the output comprises one or any combination of electrode coordinates, a visualization of the electrode coordinates, a visualization of subject's head corresponding to the imaging scan and the electrodes projected onto the head.

In one embodiment, any one of the preceding apparatuses, wherein the one or more processors are further configured by the instructions to adapt the deformable head model based on aligning vertices of the mean scalp mesh with landmarks corresponding to anatomical structures.

In one embodiment, a method is disclosed for performing the receiving, adapting, and extracting of any one of the preceding apparatuses.

In one embodiment, a non-transitory, computer readable storage medium is disclosed comprising instructions that when executed by one or more processors, causes the one or more processors to perform the receiving, adapting, and extracting of any one of the preceding apparatuses.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. Note that various combinations of the disclosed embodiments may be used, and hence reference to an embodiment or one embodiment is not meant to exclude features from that embodiment from use with features from other embodiments. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms. Any reference signs in the claims should be not construed as limiting the scope.

At least the following is claimed:

1. An apparatus, comprising:
a memory comprising instructions; and
one or more processors configured by the instructions to:
receive an average electrode file corresponding to averages of plural electrode locations;
receive a mean scalp mesh comprising a shape-constrained deformable brain model that is segmented into a set of cortical and sub-cortical brain regions, the brain model comprising a set of triangular meshes providing point-based correspondence from one subject to another;
register the average electrode locations to plural vertices of the mean scalp mesh;
enforce symmetry of the average electrode locations with respect to the mid-sagittal plane of the mean scalp mesh; and
provide as output a deformable head model comprising the mean scalp mesh encoded with the electrode locations based on the registration and enforcement for subsequent adaptation to an individual imaging scan for extraction of electrode locations specific to a respective patient by alignment of dedicated vertices of the mean scalp mesh with anatomical landmarks comprising one or more of nasion, inion, or left and right ears.

2. The apparatus of claim 1, wherein the one or more processors are further configured by the instructions to register at least a portion of the average electrode locations based on landmarks corresponding to anatomical structures.

3. The apparatus of claim 1, wherein the one or more processors are further configured by the instructions to enforce symmetry either for a subset of the registered electrode locations that are not symmetrical, by making the average electrode positions symmetric, or by making the plural vertices of the mean scalp mesh symmetric.

4. The apparatus of claim 1, wherein the one or more processors are further configured by the instructions to register the average electrode locations based on a point based rigid registration.

5. The apparatus of claim 1, wherein the one or more processors are further configured by the instructions to enforce symmetry with respect to the mid-sagittal plane of the mean scalp mesh by:
comparing corresponding electrode locations across the mid-sagittal plane; and
generating new electrode locations on the mean scalp mesh based on a half of a difference between a pair of electrode location in three dimensions.

6. The apparatus of claim 1, wherein the receiving, registering, enforcing, and providing are performed once during a training phase, and wherein at least the registering and enforcing are performed automatically.

7. The apparatus of claim 1, wherein the imaging scan comprises a magnetic resonance imaging scan of a subject, and wherein the deformable head model with encoded electrodes is based on an a priori training stage.

8. The apparatus of claim 1, wherein the one or more processors are configured by the instructions to adapt the deformable head model by deforming a mean mesh of the deformable head model to match information pertaining to the imaging scan, wherein the adapting and extracting is achieved automatically.

9. The apparatus of claim 1, wherein the one or more processors are configured by the instructions to provide an output of the electrode locations, wherein the output comprises one or any combination of electrode coordinates, a visualization of the electrode coordinates, a visualization of subject's head corresponding to the imaging scan and the electrodes projected onto the head.

10. The apparatus of claim 1, wherein the one or more processors are further configured by the instructions to adapt the deformable head model based on aligning vertices of the mean scalp mesh with landmarks corresponding to anatomical structures.

11. A method for performing the receives, the register, the enforce, and the provide of claim 1.

12. A non-transitory, computer readable medium comprising instructions that, when executed by one or more processors, causes the one or more processors to:
receive an average electrode file corresponding to averages of plural electrode locations;
receive a mean scalp mesh comprising a shape-constrained deformable brain model that is segmented into a set of cortical and sub-cortical brain regions, the brain model comprising a set of triangular meshes providing point-based correspondence from one subject to another;
register the average electrode locations to plural vertices of the mean scalp mesh;
enforce symmetry of the average electrode locations with respect to the mid-sagittal plane of the mean scalp mesh; and
provide as output a deformable head model comprising the mean scalp mesh encoded with the electrode locations based on the registration and enforcement for subsequent adaptation to an individual imaging scan for extraction of electrode locations specific to a respective patient by alignment of dedicated vertices of the mean scalp mesh with anatomical landmarks comprising one or more of nasion, inion, or left and right ears.

13. The non-transitory, computer readable medium of claim 12, wherein the instructions further cause the one or more processors to register at least a portion of the average electrode locations based on landmarks corresponding to anatomical structures.

14. The non-transitory, computer readable medium of claim 12, wherein the instructions further cause the one or more processors to enforce symmetry either for a subset of the registered electrode locations that are not symmetrical, by making the average electrode positions symmetric, or by making the plural vertices of the mean scalp mesh symmetric.

15. A computer-implemented method, comprising:
receiving an average electrode file corresponding to averages of plural electrode locations;
receiving a mean scalp mesh comprising a shape-constrained deformable brain model that is segmented into a set of cortical and sub-cortical brain regions, the brain model comprising a set of triangular meshes providing point-based correspondence from one subject to another;
registering the average electrode locations to plural vertices of the mean scalp mesh;
enforcing symmetry of the average electrode locations with respect to the mid-sagittal plane of the mean scalp mesh; and
providing as output a deformable head model comprising the mean scalp mesh encoded with the electrode locations based on the registration and enforcement for subsequent adaptation to an individual imaging scan for extraction of electrode locations specific to a respective patient by alignment of dedicated vertices of the mean scalp mesh with anatomical landmarks comprising one or more of nasion, inion, or left and right ears.

16. The computer-implemented method of claim 15, further comprising registering at least a portion of the average electrode locations based on landmarks corresponding to anatomical structures.

17. The computer-implemented method of claim 15, further comprising enforcing symmetry either for a subset of the registered electrode locations that are not symmetrical, by making the average electrode positions symmetric, or by making the plural vertices of the mean scalp mesh symmetric.

* * * * *